United States Patent
Aho et al.

(10) Patent No.: US 10,335,524 B2
(45) Date of Patent: Jul. 2, 2019

(54) PORTABLE CHEST TUBE PRESSURE AND $CO_2$ MONITOR

(71) Applicant: Mayo Foundation for Medical Education and Research, Rochester, MN (US)

(72) Inventors: Johnathon M. Aho, Rochester, MN (US); Raaj K. Ruparel, Rochester, MN (US); Phillip G. Rowse, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 153 days.

(21) Appl. No.: 15/109,883

(22) PCT Filed: Jan. 7, 2015

(86) PCT No.: PCT/US2015/010414
§ 371 (c)(1),
(2) Date: Jul. 6, 2016

(87) PCT Pub. No.: WO2015/105828
PCT Pub. Date: Jul. 16, 2015

(65) Prior Publication Data
US 2016/0325030 A1 Nov. 10, 2016

Related U.S. Application Data
(60) Provisional application No. 61/924,336, filed on Jan. 7, 2014.

(51) Int. Cl.
*A61M 1/04* (2006.01)
*A61M 1/00* (2006.01)
(Continued)

(52) U.S. Cl.
CPC ............ *A61M 1/04* (2013.01); *A61B 5/0086* (2013.01); *A61B 5/0836* (2013.01);
(Continued)

(58) Field of Classification Search
CPC .. A61M 1/0074; A61M 1/04; A61M 2205/18; A61M 2205/3303;
(Continued)

(56) References Cited

U.S. PATENT DOCUMENTS 5,005,572 A    4/1991  Raemer
5,738,656 A *  4/1998  Wagner ............... A61M 1/0084
                                                      604/119

(Continued)

FOREIGN PATENT DOCUMENTS

WO    WO2013123338 A1    8/2013

OTHER PUBLICATIONS

Anegg, Udo, et al. "AIRFIX®: the first digital postoperative chest tube airflowmetry—a novel method to quantify air leakage after lung resection." European journal of cardio-thoracic surgery 29.6 (2006): 867-872.*

(Continued)

*Primary Examiner* — Adam Marcetich
(74) *Attorney, Agent, or Firm* — Fish & Richardson P.C.

(57) ABSTRACT

Systems and methods can be used improve the efficacy of tube thoracostomy. For example, this document provides devices and methods for confirming the proper placement of a chest tube within the pleural space.

15 Claims, 2 Drawing Sheets

(51) Int. Cl.
*A61B 5/00* (2006.01)
*A61B 5/083* (2006.01)

(52) U.S. Cl.
CPC ....... *A61M 1/0074* (2013.01); *A61M 2205/18* (2013.01); *A61M 2205/3303* (2013.01); *A61M 2205/3313* (2013.01); *A61M 2205/3331* (2013.01); *A61M 2205/502* (2013.01); *A61M 2230/432* (2013.01)

(58) Field of Classification Search
CPC .. A61M 2205/3313; A61M 2205/3331; A61M 2205/502; A61M 2230/432; A61M 2210/101; A61M 2230/40; A61M 1/008; A61M 2016/0027; A61M 1/0013; A61B 5/0086; A61B 5/0836; A61B 5/08; A61B 5/746; A61B 5/0205
See application file for complete search history.

(56) References Cited

U.S. PATENT DOCUMENTS

| | | | |
|---|---|---|---|
| 5,743,259 A | 4/1998 | Kruse | |
| 6,029,076 A | 2/2000 | Fiddian | |
| 6,770,070 B1 | 8/2004 | Balbierz | |
| 8,083,684 B2 | 12/2011 | Palatnik | |
| 8,246,752 B2 | 8/2012 | Boyle | |
| 8,420,405 B2 | 4/2013 | Ostrowski | |
| 8,454,526 B2 | 6/2013 | Baker | |
| 2003/0018309 A1 | 1/2003 | Breznock | |
| 2003/0121812 A1 | 7/2003 | Sprieck | |
| 2004/0006311 A1 | 1/2004 | Shchervinsky | |
| 2004/0148140 A1* | 7/2004 | Tarassenko | A61B 5/0205 702/189 |
| 2005/0240093 A1* | 10/2005 | DeArmond | A61B 5/02042 600/372 |
| 2006/0155206 A1* | 7/2006 | Lynn | A61B 5/087 600/529 |
| 2007/0078444 A1* | 4/2007 | Larsson | A61M 1/0031 604/540 |
| 2008/0077035 A1 | 3/2008 | Baker | |
| 2009/0137911 A1* | 5/2009 | Sinderby | A61B 5/0421 600/484 |
| 2009/0264833 A1* | 10/2009 | Boyle, Jr. | B08B 9/0436 604/257 |
| 2010/0069725 A1* | 3/2010 | Al-Ali | A61B 5/0205 600/301 |
| 2010/0130947 A1* | 5/2010 | Daly | A61M 1/0023 604/318 |
| 2011/0071415 A1* | 3/2011 | Karwoski | A61B 5/08 600/529 |
| 2011/0152836 A1 | 6/2011 | Riopelle | |
| 2012/0172683 A1 | 7/2012 | Muñoz | |
| 2012/0179009 A1 | 7/2012 | Gavriely | |
| 2012/0289838 A1* | 11/2012 | Varga | A61B 5/0836 600/473 |
| 2012/0302845 A1* | 11/2012 | Lynn | A61B 5/0205 600/323 |
| 2013/0053723 A1* | 2/2013 | Leveque | A61B 5/03 600/561 |
| 2013/0104884 A1* | 5/2013 | Vazales | A61B 1/267 128/202.16 |
| 2013/0110057 A1* | 5/2013 | Croteau | A61M 1/0031 604/318 |
| 2013/0150701 A1 | 6/2013 | Budar | |
| 2013/0263855 A1* | 10/2013 | Tivig | A61B 5/4839 128/204.23 |
| 2014/0000606 A1* | 1/2014 | Doyle | A61M 16/0051 128/204.21 |
| 2014/0012096 A1* | 1/2014 | Nomura | A61B 5/746 600/301 |
| 2015/0031968 A1* | 1/2015 | Miserlis | A61M 1/0025 600/309 |
| 2017/0368241 A1 | 12/2017 | Aho et al. | |

OTHER PUBLICATIONS

Brunelli, Alessandro, et al. "Evaluation of a new chest tube removal protocol using digital air leak monitoring after lobectomy: a prospective randomised trial." European Journal of Cardio-Thoracic Surgery 37.1 (2010): 56-60.*
Bailey, "Complications of tube thoracostomy in trauma," J Accid Emerg Med., 17(2):111-114, Mar. 2000.
Pizano et al., "When should a chest radiograph be obtained after chest tube removal in mechanically ventilated patients? A prospective study," J Trauma., 53(6):1073-1077, Dec. 2002.
Raffin et al., [Assessment of end-tidal CO2 in the pleural chest tube during lung volume reduction surgery], Ann Fr Anesth Reanim., 22(5):484-486, May 2003, [Article in French] English abstract.
International Search Report and Written Opinion for PCT/US2015/010414, dated May 1, 2015, 11 pages.
International Preliminary Report on Patentability for PCT/US2015/010414, dated Jul. 21, 2016, 8 pages.

* cited by examiner

PORTABLE CHEST TUBE PRESSURE AND $CO_2$ MONITOR

CROSS REFERENCE TO RELATED APPLICATIONS

This application is a National Stage application under 35 U.S.C. § 371 of International Application No. PCT/US2015/010414, having an International Filing Date of Jan. 7, 2015, which claims the benefit of U.S. Provisional Application No. 61/924,336, file Jan. 7, 2014. The disclosure of the prior application is considered part of and is incorporated by reference in the disclosure of this application.

BACKGROUND

1. Technical Field

This document relates to systems and methods that can improve the efficacy of chest tube thoracostomy. For example, this document relates to devices and methods for confirming the proper placement of a chest tube within the pleural space.

2. Background Information

The lungs are paired organs that lie in the thoracic cavity. A gas transfer takes place in the lungs, with oxygen from inhaled air being transported into the blood, and carbon dioxide ($CO_2$) being removed from the blood. The $CO_2$ is then exhaled from the lungs.

Surrounding the lungs is a very thin space called the pleural space. The pleural space is usually very thin, and filled with a small amount of fluid. If air enters the pleural space, the lung will tend to collapse. This buildup of air in the pleural space puts pressure on the lung, so it cannot expand as much as it normally does from taking a breath. Such entrance of air into the pleural space is called a pneumothorax.

Air can enter the pleural space in various ways. If the chest wall is penetrated, which may occur as a result of an injury, air can enter the pleural space from the outside. Air can also enter from the inside, from the lung itself for example, if the lung is torn or ruptured. Another cause of pneumothorax is a pulmonary bleb. This is a weakness and out-pouching of the lung tissue, which can rupture.

Chest tubes are long, semi-stiff, clear plastic tubes that are inserted between the ribs into the chest so that they can drain collections of liquids or air from the pleural space. If the lung has been compressed because of this collection, the lung can then re-expand.

SUMMARY

This document provides systems and methods that can improve the efficacy of tube thoracostomy. For example, this document provides devices and methods for confirming the proper placement of a chest tube within the pleural space.

In general, one aspect of this document features a chest tube thoracostomy system. The chest tube thoracostomy system comprises one or more sensors that are configured to detect a level of $CO_2$ and a pressure of gas that is passing through a chest tube between a patient and a vacuum source. The chest tube thoracostomy system also comprises a monitoring device that is configured to be in electrical communication with the one or more sensors and that is configured to receive, from the one or more sensors, one or more signals that are indicative of the level of $CO_2$ and the pressure of the gas that is passing through the chest tube between the patient and the vacuum source. The monitoring device comprises a user interface that is configured to display the level of $CO_2$ and the pressure of the gas that is passing through the chest tube.

In some implementations of the chest tube thoracostomy system, the monitoring device may be configured to provide an alarm in response to the detected level of $CO_2$ or the pressure of the gas that is passing through the chest tube being outside of predetermined alarm limits. The predetermined alarm limits are programmable in some embodiments.

In a second aspect, this document features a method of confirming a desired placement of a chest tube in a pleural space of a patient. The method comprises installing a distal end portion of the chest tube in a thoracic region of the patient; attaching a proximal end portion of the chest tube to a vacuum source; installing one or more sensors in line with the chest tube, wherein the one or more sensors are configured to detect a level of $CO_2$ and a pressure of gas that is passing through the chest tube between the patient and the vacuum source; monitoring, using a monitoring device that is configured to be in electrical communication with the one or more sensors, one or more signals sent from the one or more sensors and that are indicative of the level of $CO_2$ and the pressure of the gas that is passing through the chest tube between the patient and the vacuum source, the monitoring device comprising a user interface that is configured to display the level of $CO_2$ and the pressure of the gas that is passing through the chest tube; and determining, based on a detected level of $CO_2$ and pressure of the gas that is passing through the chest tube between the patient and the vacuum source and that is indicated on the user interface of the monitoring device, whether the chest tube is placed in the pleural space as desired.

In some implementations of the method of confirming a desired placement of a chest tube in a pleural space of a patient, the method may further comprise repositioning the chest tube in relation to the pleural space in response to the level of $CO_2$ displayed by the user interface. The method may also further comprise repositioning the chest tube in relation to the pleural space in response to the level of pressure displayed by the user interface in some implementations.

Particular embodiments of the subject matter described in this document can be implemented to realize one or more of the following advantages. First, in some embodiments the systems and methods provided herein can be used to confirm whether a chest tube is properly placed within a patient's pleural space. In some circumstances, such systems and methods can provide more a definitive confirmation of proper chest tube placement than current methods. For example, chest radiographs are sometimes currently used in attempt to confirm the proper placement of chest tubes. However, such radiographical images typically provide only two-dimensional visualization. Therefore, a chest radiograph may not provide a definitive confirmation of the three-dimensional location of the chest tube within the patient's pleural space. Secondly, in some embodiments the systems and methods provided herein can be used to confirm proper chest tube placement with greater objectivity than some current techniques. For example, in another current technique used in attempt to confirm proper chest tube placement, a visual inspection of the passage of gas bubbles through a water-seal chest drainage unit is performed. However, such visual inspection is inherently subjective and prone to human error. In contrast, in some embodiments the systems and methods provided herein allow for objective detection and quantification of the proper placement of chest tubes by monitoring $CO_2$ extracted from the pleural space. Further, in some embodiments the systems and methods provided herein allow for objective detection and quantification of the proper placement of chest tubes by monitoring the pressure within the chest tube. Third, in some embodiments the systems and methods provided herein can assist with a determination of whether an air leak is an internal or an external air leak.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

This document provides systems and methods that can improve the efficacy of tube thoracostomy. For example, this document provides devices and methods for confirming the proper placement of a chest tube within the pleural space.

Pneumothorax (air in the pleural space) can be life-threatening. The immediate treatment for pneumothorax is tube thoracostomy, or the insertion of a chest tube. A long, flexible, hollow, narrow tube is inserted through the ribs into the pleural space, and the tube is attached to a suction device. This allows the air to be evacuated from the pleural space, and allows the lung to re-expand. Chest tubes are generally inserted using local anesthesia. The chest tube is left in place until the lung leak seals on its own, which usually occurs within two to five days.

Some pneumothorax conditions can be characterized by the presence of $CO_2$ in the air within the pleural space. For example, when a lung is punctured, some of the air that is exhaled from the lung will escape into the pleural space. In that circumstance, $CO_2$ from the exhaled air will be present within the pleural space. When a chest tube thoracostomy system is used in that scenario to treat pneumothorax, $CO_2$ will be present in the gas that is removed from the pleural space by the chest tube. Therefore, the presence of $CO_2$ in the gas removed by the chest tube can be indicative of a chest tube that is properly placed so as to remove gas from the pleural space.

Figure 1:
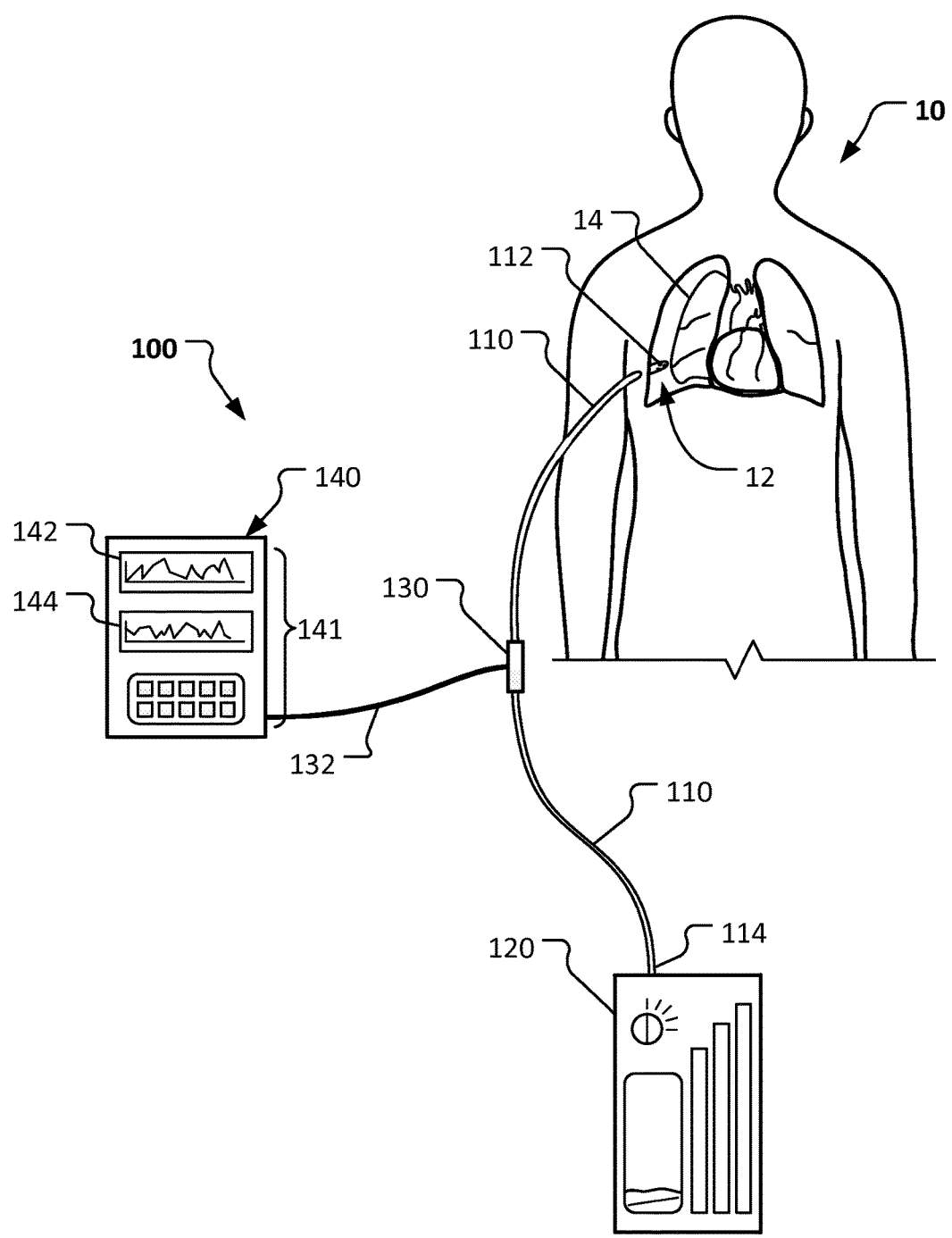
FIG. 1 is a schematic diagram of patient undergoing a chest tube thoracostomy using a tube thoracostomy monitor system in accordance with some embodiments provided herein.

Referring to FIG. 1, a patient 10 is undergoing a tube thoracostomy procedure using a tube thoracostomy system 100. Tube thoracostomy system 100 includes a chest tube 110, a suction source such as a water-seal chest drainage unit (CDU) 120, an in-line sensor module 130 and a monitor 140.

Chest tube 110 is inserted into patient 10 and positioned so that a distal end portion 112 of chest tube 110 is in a pleural space 12 near a partially collapsed lung 14 of patient 10. Distal end portion 112 includes one or more fenestrations so that the lumen of chest tube 110 is in fluid communication with pleural space 12. A proximal end portion 114 of chest tube 110 is connected to CDU 120. CDU 120 provides a source of suction that is conveyed through chest tube 110 to assist with evacuation of air from pleural space 12. In some embodiments, in-line sensor module 130 is positioned in a confluent relationship with chest tube 110, and between patient 10 and CDU 120. Monitor 140 is electrically connected to in-line sensor module 130 via a cable 132. Monitor 140 includes a user interface 141.

In some embodiments, in-line sensor module 130 and monitor 140 are configured to sense $CO_2$ in chest tube 110. The measurement of $CO_2$ can be displayed on a $CO_2$ readout 142 of user interface 141 located on monitor 140. $CO_2$ readout 142 can be observed and monitored by a clinician to confirm whether there is $CO_2$ present in the gas that is being evacuated from pleural space 12 of patient 10. In some circumstances, the clinician can thereby confirm whether chest tube 110 is properly positioned within pleural space 12.

It should be understood that tube thoracostomy system 100 can include one or more sensors for measuring the $CO_2$ content (e.g., in-line sensor module 130) that can be positioned at various locations relative to patient 10 and/or relative to tube thoracostomy system 100. For example, in some embodiments tube thoracostomy system 100 can be configured to perform mainstream $CO_2$ monitoring. In some embodiments, tube thoracostomy system 100 can be configured to perform sidestream $CO_2$ monitoring. Accordingly, one or more $CO_2$ content sensors can be positioned at locations such as, but not limited to, directly in chest tube 110, within monitor 140, within CDU 120, and/or within other tubes or devices of tube thoracostomy system 100.

In some embodiments, infrared spectroscopy is used to measure the $CO_2$ content of the gas in chest tube 110 of tube thoracostomy system 100. Infrared spectroscopy works on the principle that $CO_2$ absorbs infra-red radiation. A beam of infra-red light can be passed across the gas within in-line sensor module 130 to fall on a photo sensor located in in-line sensor module 130. The presence of $CO_2$ in the gas leads to a reduction in the amount of a specific wavelength of light falling on the photo sensor, which changes the voltage in a circuit located in monitor 140. The measured amount of $CO_2$ can then be indicated on $CO_2$ readout 142 located on monitor 140. In some embodiments, other methods of detecting the presence of $CO_2$ are used by in-line sensor module 130 and monitor 140.

In the event of an internal air leak, such as from a puncture of lung 14, $CO_2$ will typically be present within pleural space 12. Consequently, if chest tube 110 is properly positioned within pleural space 12, $CO_2$ would be expected to be present in chest tube 110 at in-line sensor module 130. When $CO_2$ is in chest tube 110 at in-line sensor module 130, the $CO_2$ will be detected by the aforementioned operations of in-line sensor module 130 and monitor 140. Therefore, when a clinician operator observes that monitor 140 indicates the presence of $CO_2$ in chest tube 110, the proper positioning of chest tube 110 in pleural space 12 is thereby confirmed.

Conversely, if chest tube 110 is not properly placed within pleural space 12, $CO_2$ may not be present within chest tube 110 at in-line sensor module 130. Therefore, when a clinician operator observes that monitor 140 does not indicate the presence of $CO_2$ in chest tube 110, the clinician operator may use such information to further investigate whether chest tube 110 is properly positioned within pleural space 12.

In some embodiments, in-line sensor module 130 and monitor 140 are configured to sense the pressure in chest tube 110. The measurement of pressure can be indicated on a pressure readout 144 of user interface 141 located on monitor 140. Pressure readout 144 can be observed and monitored by a clinician to confirm whether the pressure in chest tube 110 indicates that gas is being evacuated from pleural space 12 of patient 10 in an expected manner. In some circumstances, the clinician can thereby confirm whether chest tube 110 is properly positioned within pleural space 12.

If chest tube 110 is improperly placed in patient 10, in some circumstances the pressure in chest tube 110 at in-line sensor module 130 will be indicative of the improper placement. In one such example, a pressure in chest tube 110 that is lower than expected may indicate an improper placement of chest tube 110. If, for example, distal end portion 112 of chest tube 110 is positioned within subcutaneous fat of patient 10, rather than in pleural space 12, the pressure within chest tube 110 will be lower than if distal end portion 112 is positioned in pleural space 12. In that situation, a clinician operator may observe the low pressure indicated by pressure readout 144 located on monitor 140 and be prompted to further investigate to determine whether chest tube 110 is properly positioned in pleural space 12.

In another example scenario, a higher than expected pressure in chest tube 110 may be used as an indicator of an improperly placed chest tube 110. For example, if ambient air is leaking into chest tube 110 because one or more fenestrations of distal end portion 112 are exposed to ambient air, the pressure within chest tube 110 will be slightly higher than if distal end portion 112 is properly positioned in pleural space 12. A clinician operator may then observe the higher than expected pressure indicated by pressure readout 144 located on monitor 140 and be prompted to further investigate to determine whether chest tube 110 is properly positioned in pleural space 12.

The pressure and $CO_2$ monitoring capabilities of tube thoracostomy system 100 may be used in conjunction with each other in some embodiments. For example, in some circumstances, when a particular pressure is detected in chest tube 110, an amount of $CO_2$ within a particular range may be expected. In such cases, monitor 140 may include a processor running an algorithm that uses a pressure as an input to determine an expected range of $CO_2$.

In some embodiments, monitor 140 may provide an alarm when the pressure or $CO_2$ within chest tube 110 are outside of expected predetermined levels. In particular embodiments, alarm limits may be programmable by a clinician operator.

Figure 2:
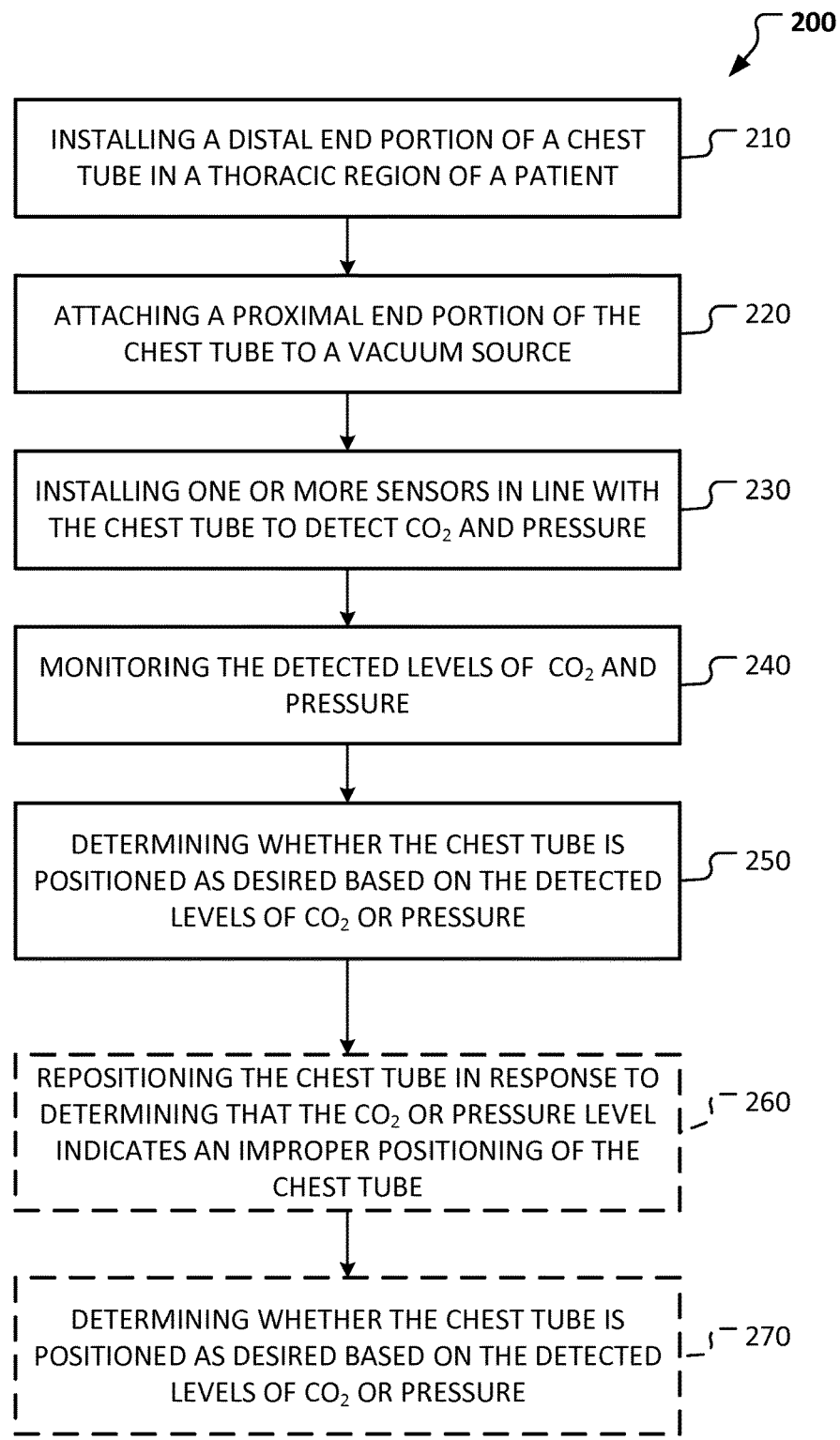
FIG. 2 is a flowchart of a method for confirming proper placement of a chest tube in a pleural space in accordance with some embodiments provided herein.

With reference to FIG. 2, a method 200 for confirming a desired placement of a chest tube in a pleural space of a patient in accordance with some embodiments provided herein is presented. Method 200 can utilize a medical device system such as the tube thoracostomy system 100 described above.

At operation 210, a distal end portion of a chest tube is installed in a thoracic region of the patient. The desired location within the thoracic region is the pleural space. The installation may be, for example, part of a treatment procedure for a condition such as a punctured lung. In some cases, an internal air leak from the lung or bronchi may be suspected.

At operation 220, a proximal end portion of the chest tube is attached to a vacuum source. In some cases, a CDU may be used as the vacuum source. In some cases, another type of vacuum source may be used.

At operation 230, one or more sensors are installed in line with the chest tube. The one or more sensors are configured to be responsive to a level of $CO_2$ and a pressure of gas that is passing through the chest tube between the patient and the vacuum source.

At operation 240, the levels of $CO_2$ and pressure of the gas that is passing through the chest tube between the patient and the vacuum source is monitored. The monitoring may be performed using a monitoring device that is configured to be in electrical communication with the one or more sensors. The one or more sensors may send one or more signals to the monitoring device that are indicative of the level of $CO_2$ and the pressure of the gas that is passing through the chest tube between the patient and the vacuum source. The monitoring device may comprise a user interface that is configured to display the level of $CO_2$ and the pressure of the gas that is passing through the chest tube.

At operation 250, a determination is made as to whether the chest tube is placed in the pleural space as desired. The determination is made at least partly based on the detected level of $CO_2$ and pressure of the gas that is passing through the chest tube between the patient and the vacuum source, and that is indicated on the user interface of the monitoring device.

At operation 260, the chest tube is optionally repositioned in relation to the pleural space in response to the level of $CO_2$ or pressure displayed by the user interface of the monitoring device. For example, if the level of $CO_2$ is below an expected threshold level, a determination may be made that the chest tube needs to be repositioned. In another example, if the level of negative pressure (vacuum) is more negative than expected, a determination may be made that the chest tube needs to be repositioned. In yet another example, if a combination of $CO_2$ and pressure of the gas that is passing through the chest tube between the patient and the vacuum source and that is indicated on the user interface of the monitoring device is different than expected, a determination may be made that the chest tube needs to be repositioned.

At operation 270, a redetermination is optionally made as to whether the chest tube is placed in the pleural space as desired. The redetermination is made at least partly based on a detected level of $CO_2$ and pressure of the gas that is passing through the chest tube between the patient and the vacuum source and that is indicated on the user interface of the monitoring device after the repositioning of operation 260. If necessary, operations 260 and 270 can be repeated until the positioning of the chest tube in relation to the patient is as desired.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A chest tube thoracostomy system comprising:
   one or more sensors that are configured to detect a level of $CO_2$ and a pressure of gas that is passing through a chest tube between a patient and a vacuum source; and
   a monitoring device that is configured to be in electrical communication with the one or more sensors and that is configured to receive, from the one or more sensors, one or more signals that are indicative of the detected level of $CO_2$ and the detected pressure of the gas that is passing through the chest tube between the patient and the vacuum source, the monitoring device comprising a user interface that is configured to display indications of the detected level of $CO_2$ and the detected pressure,
   wherein the monitoring device is configured to algorithmically process the one or more signals that are indicative of: (i) the detected level of $CO_2$ and (ii) the detected pressure in combination with each other to enable determining whether the chest tube needs to be repositioned within the patient.

2. The chest tube thoracostomy system of claim 1, wherein the monitoring device is configured to provide an alarm in response to the detected level of $CO_2$ or the pressure of the gas that is passing through the chest tube being outside of alarm limits.

3. The chest tube thoracostomy system of claim 2, wherein the alarm limits are programmable.

4. The chest tube thoracostomy system of claim 2, wherein the monitoring device is configured to provide an alarm in response to the detected level of $CO_2$, and wherein the alarm limits are based on the detected pressure of the gas.

5. The chest tube thoracostomy system of claim 1, further comprising the chest tube.

6. The chest tube thoracostomy system of claim 5, wherein the chest tube includes one or more fenestrations.

7. The chest tube thoracostomy system of claim 1, further comprising the vacuum source, and wherein the vacuum source is a water-seal chest drainage unit.

8. The chest tube thoracostomy system of claim 1, wherein at least one of the one or more sensors is configured to detect $CO_2$ using infra-red spectroscopy.

9. A method of confirming a desired placement of a chest tube in a pleural space of a patient, the method comprising:
   installing a distal end portion of the chest tube in a thoracic region of the patient;
   attaching a proximal end portion of the chest tube to a vacuum source;
   installing one or more sensors in line with the chest tube, wherein the one or more sensors are configured to detect a level of $CO_2$ and a pressure of gas that is passing through the chest tube between the patient and the vacuum source;
   monitoring, using a monitoring device that is configured to be in electrical communication with the one or more sensors, one or more signals sent from the one or more sensors and that are indicative of a detected level of $CO_2$ and a detected pressure of the gas that is passing through the chest tube between the patient and the vacuum source, the monitoring device comprising a user interface that is configured to display indications of the detected level of $CO_2$ and the detected pressure; and
   determining, based on a combination of: (i) the detected level of CO2 and (ii) the detected pressure, whether the chest tube is placed to communicate effectively with the pleural space.

10. The method of claim 9, further comprising repositioning the chest tube in relation to the pleural space in response to the indication of the level of $CO_2$ displayed by the user interface.

11. The method of claim 9, issuing an alarm, by the monitoring device, based on the detected level of $CO_2$ being outside of alarm limits.

12. The method of claim 9, further comprising repositioning the chest tube in relation to the pleural space in response to the indication of the level of pressure displayed by the user interface.

13. The method of claim 9, issuing an alarm, by the monitoring device, based on the detected level of pressure being outside of alarm limits.

14. The method of claim 9, further comprising evacuating air from the thoracic region of the patient through the chest tube.

15. The method of claim 9, further comprising repositioning the chest tube in relation to the pleural space in response to determining, based on the combination of: (i) the detected level of $CO_2$ and (ii) the detected pressure, that the chest tube is not placed in the pleural space as desired.

* * * * *